(12) United States Patent
LaPlante et al.

(10) Patent No.: US 9,254,220 B1
(45) Date of Patent: Feb. 9, 2016

(54) METHOD AND SYSTEM FOR ASSESSING SEVERITY AND STAGE OF PERIPHERAL ARTERIAL DISEASE AND LOWER EXTREMITY WOUNDS USING ANGIOSOME MAPPING

(71) Applicant: Vasamed, Inc., Eden Prairie, MN (US)

(72) Inventors: Paulita M. LaPlante, Inner Grove Heights, MN (US); Daniel J. Bartnik, Eden Prairie, MN (US); Rose A. Griffith, Eden Prairie, MN (US)

(73) Assignee: VASAMED, INC., Eden Prairie, MN (US)

( * ) Notice: Subject to any disclaimer, the term of this patent is extended or adjusted under 35 U.S.C. 154(b) by 576 days.

(21) Appl. No.: 13/573,989

(22) Filed: Oct. 18, 2012

Related U.S. Application Data

(63) Continuation-in-part of application No. 12/321,813, filed on Jan. 26, 2009, now abandoned, which is a continuation-in-part of application No. 12/021,938, filed on Jan. 29, 2008, now Pat. No. 8,133,177, and a (Continued)

(51) Int. Cl.
*A61B 19/00* (2006.01)
*A61B 5/02* (2006.01)
*A61F 5/56* (2006.01)

(52) U.S. Cl.
CPC ..................................... *A61F 5/566* (2013.01)

(58) Field of Classification Search
CPC ........... A61B 5/14532; A61B 5/14546; A61B 5/1473; A61B 5/14865; A61B 5/1486; A61B 5/026

USPC ........... 600/306, 363, 345, 504; 128/897–899
See application file for complete search history.

(56) References Cited

U.S. PATENT DOCUMENTS

| 3,511,227 A | 5/1970 | Johnson |
| 3,905,889 A | 9/1975 | Macur et al. |

(Continued)

FOREIGN PATENT DOCUMENTS

| WO | WO 94/23645 | 4/1994 |
| WO | WO 98/20794 | 5/1998 |

(Continued)

OTHER PUBLICATIONS

D. Mukherjee, K. Munir, A.T. Hirsch, S. Chetcuti, P.M. Grossman and S. Rajagopalan, et al. Development of a multicenter peripheral arterial interventional database: the PVD-QI2. Am Heart J, 149 (2005), pp. 1003-1008.*

(Continued)

*Primary Examiner* — Christine H Matthews
*Assistant Examiner* — Sunita Reddy
(74) *Attorney, Agent, or Firm* — Barbara A. Wrigley; Oppenheimer Wolff & Donnelly LLP

(57) ABSTRACT

The present invention provides a system for assessing the severity and stage of PAD including at least one sensor that measures skin perfusion pressure; a knowledge base that provides data on lower extremity angiosomes; and a processing device in operable communication with the sensor and the knowledge base, the processing device that outputs a visual representation of at least one of the lower extremity angiosomes that guides the sensor in the mapping of a testing site relative to a target vessel where the skin perfusion pressure measurement will be taken.

9 Claims, 10 Drawing Sheets
(3 of 10 Drawing Sheet(s) Filed in Color)

Related U.S. Application Data continuation-in-part of application No. 11/468,203, filed on Aug. 29, 2006, now Pat. No. 7,736,311.

(60) Provisional application No. 61/062,476, filed on Jan. 25, 2008.

(56) References Cited

U.S. PATENT DOCUMENTS

| | | |
|---|---|---|
| 4,016,863 A | 4/1977 | Brantigan |
| 4,109,647 A | 8/1978 | Stern et al. |
| 4,155,354 A | 5/1979 | Rasmussen |
| 4,228,805 A | 10/1980 | Rosen et al. |
| 4,230,122 A | 10/1980 | Lubbers et al. |
| 4,324,258 A | 4/1982 | Huebscher et al. |
| 4,381,011 A | 4/1983 | Somers, III |
| 4,503,859 A | 3/1985 | Petty |
| 4,535,786 A | 8/1985 | Kater |
| 4,538,618 A | 9/1985 | Rosenberg et al. |
| 4,577,109 A | 3/1986 | Hirschfeld |
| 4,590,948 A | 5/1986 | Nilsson |
| 4,593,698 A | 6/1986 | Athans |
| 4,596,254 A | 6/1986 | Adrian et al. |
| 4,632,119 A | 12/1986 | Reichstein |
| 4,643,192 A | 2/1987 | Fiddian-Green |
| 4,729,384 A | 3/1988 | Bazenet |
| 4,729,824 A | 3/1988 | Gilner |
| 4,759,374 A | 7/1988 | Kierney et al. |
| 4,785,814 A | 11/1988 | Kane |
| 4,789,453 A | 12/1988 | Eberhard et al. |
| 4,800,886 A | 1/1989 | Nestor |
| 4,816,131 A | 3/1989 | Bomsztyk |
| 4,833,091 A | 5/1989 | Leader |
| 4,834,101 A | 5/1989 | Collison |
| 4,842,783 A | 6/1989 | Blaylock |
| 4,890,619 A | 1/1990 | Hatschek |
| 4,892,383 A | 1/1990 | Klainer et al. |
| 4,919,891 A | 4/1990 | Yafuso et al. |
| 4,945,896 A | 8/1990 | Gade |
| 4,966,148 A | 10/1990 | Millar |
| 4,981,470 A | 1/1991 | Bombeck, IV |
| 5,006,314 A | 4/1991 | Gourley et al. |
| 5,098,659 A | 3/1992 | Yim et al. |
| 5,105,812 A | 4/1992 | Corman |
| 5,117,827 A | 6/1992 | Stuebe et al. |
| 5,158,083 A | 10/1992 | Sacristan et al. |
| 5,166,990 A | 11/1992 | Riccitelli et al. |
| 5,174,290 A | 12/1992 | Fiddian-Green |
| 5,251,619 A | 10/1993 | Lee |
| 5,280,548 A | 1/1994 | Atwater et al. |
| 5,297,556 A | 3/1994 | Shankar |
| 5,329,922 A | 7/1994 | Atlee |
| 5,330,718 A | 7/1994 | Hui et al. |
| 5,341,803 A | 8/1994 | Goldberg |
| 5,368,027 A | 11/1994 | Lubbers et al. |
| 5,408,999 A | 4/1995 | Singh et al. |
| 5,411,022 A | 5/1995 | McCue |
| 5,423,320 A | 6/1995 | Salzman et al. |
| 5,453,248 A | 9/1995 | Olstein |
| 5,456,251 A | 10/1995 | Fiddian-Green |
| 5,479,923 A | 1/1996 | Rantala |
| 5,536,783 A | 7/1996 | Olstein et al. |
| 5,579,763 A | 12/1996 | Weil et al. |
| 5,596,988 A | 1/1997 | Markle et al. |
| 5,607,644 A | 3/1997 | Olstein et al. |
| 5,620,000 A | 4/1997 | Zinser et al. |
| 5,631,340 A | 5/1997 | Olstein |
| 5,672,515 A | 9/1997 | Furlong |
| 5,714,121 A | 2/1998 | Alderete et al. |
| 5,743,259 A | 4/1998 | Kruse |
| 5,778,878 A | 7/1998 | Kellam |
| 5,788,631 A | 8/1998 | Fiddian-Green |
| 6,055,447 A | 4/2000 | Weil et al. |
| 6,178,342 B1 | 1/2001 | Borgos et al. |
| 6,254,628 B1 | 7/2001 | Wallace |
| 6,258,046 B1 | 7/2001 | Kimball et al. |
| 6,501,973 B1 | 12/2002 | Foley et al. |
| 6,930,608 B2 | 8/2005 | Grajales et al. |
| 7,736,311 B2 * | 6/2010 | Bartnik et al. ............... 600/363 |
| 8,133,177 B2 | 3/2012 | LaPlante et al. |
| 2002/0168618 A1 | 11/2002 | Anderson et al. |
| 2003/0214408 A1 | 11/2003 | Grajales et al. |
| 2004/0127800 A1 | 7/2004 | Anderson et al. |
| 2005/0079147 A1 | 4/2005 | Delaey et al. |
| 2006/0052686 A1 | 3/2006 | Zhang et al. |
| 2006/0064800 A1 * | 3/2006 | Freund ............................ 2/446 |
| 2006/0287603 A1 | 12/2006 | Bartnik et al. |
| 2007/0016079 A1 | 1/2007 | Freeman et al. |
| 2007/0038042 A1 * | 2/2007 | Freeman et al. ............. 600/310 |
| 2007/0051889 A1 * | 3/2007 | Yannacone, Jr. et al. ..... 250/330 |
| 2007/0128174 A1 * | 6/2007 | Kleinsek et al. ............. 424/93.7 |
| 2007/0173727 A1 | 7/2007 | Naghavi et al. |
| 2007/0225606 A1 * | 9/2007 | Naghavi et al. ............... 600/438 |
| 2007/0225614 A1 | 9/2007 | Naghavi et al. |
| 2008/0183059 A1 | 7/2008 | LaPlante et al. |
| 2014/0012108 A1 * | 1/2014 | McPeak ........................ 600/324 |

FOREIGN PATENT DOCUMENTS

| | | |
|---|---|---|
| WO | WO 00/59372 | 10/2000 |
| WO | WO 2005/030038 | 4/2005 |

OTHER PUBLICATIONS

Benazzo et al., "Endothelin-Induced Vasoconstriction in Rabbit Nasal Mucosa," *Acta Otolaryngol* (Stockh), vol. 114(5), pp. 544-546 (1994).

Bertuglia et al., "Venular Oscillatory Flow During Hemorrhagic Shock and No Inhibition in Hamster Cheek Pouch Microcirculation," *Microvascular Research*, vol. 54, pp. 23-242 (1997).

Casasco et al., "Occurrence, Distribution and Possible Role of the Regulatory Peptide Endothelin in the Nasal Mucosa," *Cell & Tissue Research*, vol. 274(2), pp. 241-247 (1993).

Friberg et al., "Habitual Snorers and Sleep Apnoics Have Abnormal Vascular Reactions of the Soft Palatal Mucosa on Afferent Nerve Stimulation," *The Laryngoscope*, vol. 108(3), pp. 431-436 (1998).

Grudemo et al., "Rhinostereometry and Laser Doppler Flowmetry in Human Nasal Mucosa: Changes in Congestion and Microcirculation During Intranasal Histamine Challenge," *ORL*, vol. 59, pp. 50-56 (1997).

Grudemo et al., "Studies of Spontaneous Fluctuations in Congestion and Nasal Mucosal Microcirculation and the Effects of Oxymetazoline Using Rhinostereometry and Micromanipulator Guided Laser Doppler Flowmetry," *American Journal of Rhinology*, vol. 13(1), pp. 1-6 (1999).

Hoke et al., "Blood-Flow Mapping of Oral Tissues by Laser Doppler Flowmetry," *International Journal of Oral & Maxillofacial Surgery*, vol. 23(5), pp. 312-315 (1994).

Jin et al., "Decreases in Organ Blood Flows Associated with Increase in Sublingual $PCO_2$ During Hemorrhagic Shock," *J. Applied Physiol.*, vol. 85(6), pp. 2360-2364 (1998).

Kelley et al., "Comparison Between the Uptake of Nitrous Oxide and Nitric Oxide in the Human Nose," *Journal of Applied Physiology*, vol. 85(4), pp. 1203-1209 (1998).

Klinger et al., "Untersuchungen zur Mikro-zirkulation der Nasenschleimhaut bei Verwendung von Ballon-tamponaden," ("The Influence of Cuffed Epistaxis Catheters on Nasal Mucosa Blood Flow Measured by Laser Doppler Flowmety") *Laryngo-Rhino-Otologie*, vol. 76, pp. 127-130 (1997).

Lacroix et al., "Sympathetic Vascular Control of the Pig Nasal Mucosa (III): Co-Release of Noradrenaline and Neuropeptide Y," *Acta Physiologica Scandinavica*, vol. 135(1), pp. 17-28 (1989).

Marais et al., "A Preliminary Comparison of the Effects of Halothane and Isoflurane on Nasal Mucosal Blood Flow," *Rhinology*, vol. 31(1), pp. 31-83 (1993).

Weaver et al., "Effect of Internal Maxillary Arterial Occlusion on Nasal Blood Flow in Swine," *The Laryngoscope*, vol. 109(1), pp. 8-14 (1999).

Ylipaavalniemi et al., "Effect of Local Anaesthesia on the Blood Perfusion of Oral Mucosa Measured by the Laser Doppler Method," *Proceedings of the Finnish Dental Society*, vol. 79(2), pp. 58-61 (1983).

(56) References Cited

OTHER PUBLICATIONS

Jin et al. (1997), "End-Tidal $PCO_2$ Serves as an Indicator of Cardiac Output During Experimental Septic Shock," *Crit. Care Med.* 25(1):A122 (Abstract).

Nakagawa et al. (1997), "Sublingual Capnometry for Quantitation of the Severity of Hemorrhagic Shock," *Shock* 7:14 (Abstract).

Nakagawa et al. (1997), "$ETCO_2$ as Non-Invasive Indicator of Cardiac Output During Hemorrhagic Shock," *Crit. Care Med.* 25(1):A132 (Abstract).

Nakagawa et al. (1997) et al. (1997), "Sublingual Capnography as an Indicator of Perfusion Failure in Human Patients," *Chest* 112:4S (Abstract).

Nakagawa et al. (1998), "Comparison of Sublingual Capnometry with Gastric Capnometry and Lactate as Indicators of the Severity of Hemorrhagic Shock," *Crit. Care Med.* 26(1):A44 (Abstract).

Ogino et al. (1994), "Reflectance Pulse Oximeter Measuring Central $SaO2$ From Mouth," Proceedings of the Annual International Conference of the IEEE Engineering in Medicine and Biology Society, Baltimore, 2(16):914-915.

Peterson et al. (1984), "Fiber Optic Sensors for Biomedical Applications," *Science* 224(4645):123-127.

Sato et al. (1997), "Espohageal and Gastric $PCO_2$ Both Serve as Quantitative Indicators of Organ Blood Flow During Hemorrhagic Shock," *Crit. Care Med.* 25(1):A37 (Abstract).

Sato et al. (1997), "Esophageal $PCO_2$ as a Monitor of Perfusion Failure During Hemorrhagic Shock," *Appl. Physiol.* 82(2):558-562.

Seitz (1984), "Chemical Sensors Based on Fiber Optics," *Anal. Chem.* 56(1):16A-34A.

Tang et al. (1988), "Myocardial Preservation During Cardiopulmonary Resuscitation," *Curr. Opin. Crit. Care* 4:155-160.

Vurek et al. (1983), "A Fiber Optic $PCO_2$ Sensor," *Annals Biomed. Engineer* 11:499-510.

Weil (1998), "The Assault on the Swan-Ganz Catheter," *Chest* 113:1379-1386 (1998) (Invited Publication).

Xie et al. (1997) "Sublingual Capnometry for Quantitation of the Severity of Septic Shock," *Shock* 7:13-14 (Abstract).

Vlad-Adrian Alexandrescu, M.D., et al., Selective Primary Angioplasty Following an Agiosome Model of Reperfusion in the Treatment of Wagner 1-4 Diabetic Foot Lesions: Practice in Multidisciplinary Diabetic Limb Service, J Endovasc Ther., 2008, pp. 580-593, vol. 15, International Society of Endovascular Specialists, Belgium.

Richard F. Neville, et al., Revascularization of a Specific Angiosome for Limb Salvage: Does the Target Artery Matter? Annals of Vascular Surgery, 2008, pp. 1-7, Elsevier, USA.

Mukherjee, K. Munir, et al.; Development of a Multicenter Peripheral Arterial Interventional Database: the PVD-Q12. Am Heart J., 149 (2005), pp. 1003, 1008.

\* cited by examiner

METHOD AND SYSTEM FOR ASSESSING SEVERITY AND STAGE OF PERIPHERAL ARTERIAL DISEASE AND LOWER EXTREMITY WOUNDS USING ANGIOSOME MAPPING

CROSS-REFERENCE TO RELATED APPLICATIONS

This application is a continuation in part of U.S. application Ser. No. 12/321,813, abandoned, which claims the benefit of priority to U.S. Prov. Appln. Ser. No. 61/062,476 filed Jan. 25, 2008 and which is a continuation in part of U.S. Appln. Ser. No. 12/021,938 filed Jan. 29, 2008, now U.S. Pat. No. 8,133,177, and a continuation in part of U.S. Appln. Ser. No. 11/468,203 filed Aug. 29, 2006, now U.S. Pat. No. 7,736, 311. The entireties of all of the foregoing applications are hereby incorporated by reference.

COPYRIGHT

A portion of the disclosure of this patent document contains material which is subject to copyright protection. The copyright owner has no objection to the facsimile reproduction by anyone of the patent document or the patent disclosure, as it appears in the Patent and Trademark Office file or records, but otherwise reserves all copyright rights whatsoever.

FIELD OF THE INVENTION

This invention relates generally to a method and system for assessing the severity and stage of peripheral arterial disease and lower extremity wounds using angiosome mapping.

BACKGROUND OF THE INVENTION

Atherosclerotic disease is widespread but commonly associated only with coronary heart disease. However, atherosclerosis of the peripheral vascular system, e.g. in the lower extremities, also contributes to significant morbidity and mortality in patients. Peripheral arterial disease (PAD), includes all diseases caused by the obstruction of large arteries in the arms and legs. PAD can result from atherosclerosis, inflammatory processes leading to stenosis, an embolism or thrombus formation. It causes either acute or chronic ischemia (lack of blood supply), typically of the legs. Lower extremity occlusive PAD can be defined on the basis of anatomical or functional considerations. Anatomically it is defined as atherosclerotic arterial disease, while functionally it is defined as arterial narrowing, causing a mismatch between the oxygen supply and demand resulting in symptoms of intermittent claudication (IC), exercise limitations, or tissue loss. These two definitions help divide PAD into asymptomatic and symptomatic disease states.

Worldwide, the prevalence of peripheral vascular disease in people 55 years of age is 10%-25% and steadily increases with age. Over 70%-80% of affected individuals are asymptomatic. In the United States, peripheral arterial disease affects from 12% to 20% of Americans age 65 and older. Despite its prevalence and cardiovascular risk implications, only 25% of PAD patients undergo treatment principally due to lack of diagnosis. However, diagnosis is critical, as people with PAD have a four to five times higher risk of heart attack and/or stroke. Thus, the prognosis for patients with PAD is poor.

Several of the present inventors have collaborated on developing a novel instrument that measures skin perfusion pressure as more particularly described in U.S. Publn. Nos. 2006/0287603 and 2008/0183059. Briefly, the novel instrument measures skin perfusion pressure (SPP), which assists the physician in assessing a patient's micro-circulatory health. The instrument utilizes laser Doppler to evaluate reactive hyperemia, the transient increase in organ or limb blood flow following a brief period of occlusion, by measuring in millimeters of mercury the pressure at which blood flow first returns to capillaries following controlled occlusive release. This generates an SPP value. The instrument also assesses macro-circulatory health by utilizing air plethysmography to evaluate changes in arterial blood volume with each cardiac cycle to generate a pulse volume recording (PVR); these waveforms are rated according to severity ranging from "likely severely abnormal" to "likely normal." Alone or together, SPP and PVR may be used to assess the severity and stage of peripheral arterial disease and the potential for wound healing. However, because the diagnosis of peripheral arterial disease is critical the present inventors have developed improvements to the system using angiosome mapping that existing scoring systems, such as Fontaine Stages, Rutherford Category, S(AD) Foot Ulcer Classification, Wagner Scale for wound classification and the like, are unable to objectify.

Angiosomes are three dimensional blocks of tissue supplied by a single "source" artery. Dr. Ian Taylor, expanding on the work of previous anatomists, conducted a landmark anatomic study that detailed the angiosome principal and identified over 40 angiosomes of the body. Dr. Christopher Attinger further investigated angiosomes of the foot and ankle for their impact on limb salvage, specifically in relation to incision planning, blood flow preservation, tissue reconstruction, and revascularization procedures to afford optimal healing of wounds in ischemic limbs. Knowledge of the angiosome principal is frequently utilized by plastic surgeons wherein detailed and specific understanding of vascular sources to skin tissue is critical to successful outcome for the patient. However, knowledge of the angiosome principal is not well understood within other medical disciplines.

One such area is the management of PAD, critical limb ischemia (CLI) and diabetic (DM) foot where there are six distinct angiosomes. The six angiosomes of the foot and ankle originate from the three main arteries to the foot and ankle. The posterior tibial artery supplies the medial ankle and the plantar foot, the anterior tibial artery supplies the dorsum of the foot, and the peroneal artery supplies the anterolateral ankle and the lateral rear foot. The large angiosomes of the foot can be further broken into angiosomes of the major branches of the above arteries. The three main branches of the posterior tibial artery each supply distinct portions of the plantar foot: the calcaneal branch (heel), the medial plantar artery (instep), and the lateral plantar artery (lateral midfoot and forefoot). The two branches of the peroneal artery supply the anterolateral portion of the ankle and rear foot, the anterior perforating branch (lateral anterior upper ankle) and the calcaneal branch (plantar heel). The anterior tibial artery supplies the anterior ankle and then becomes the dorsalis pedis artery that supplies the dorsum of the foot.

Angiosomes are inherently three-dimensional. Currently, however, angiosome concepts are communicated by presenting a combination of two-dimensional flat images and/or flat illustrations of anatomical vasculature. Further, existing representations for angiosomes are not integrated into systems for assessing PAD, CLI or DM conditions. Moreover current use of angiosome concepts, if any, is limited to the subjective interpretation of combined sets of data by the physician.

There is a need to provide health care professionals with a method and system to visually represent lower extremity angiosomes to guide the placement of a skin perfusion sensor and map a testing site relative to a target vessel in the angiosome. A skin perfusion measurement, which is based on the aforementioned angiosome mapping, will enable an accurate assessment of severity and stage of peripheral arterial disease and lower extremity wound healing potential. There is a further need to provide expanded utility with regard to angiosome mapping in identifying a medical condition to objectify changes to skin, pallor, temperature, etc. An additional need is to incorporate angiosome mapping with functional markers and other clinical indices to provide a PAD, CLI and/or wound healing evaluation system. The inclusion of angiosomes brings new perspective to the anatomical and functional considerations that inform education, diagnosis, therapeutic management and communication applications.

BRIEF SUMMARY OF THE INVENTION

The foregoing invention overcomes the problems and disadvantages of current methods that subjectively assess the severity and stage of peripheral arterial disease and lower extremity wounds.

The present invention combines mechanical measurements such as flow, which includes blood flow, fluid flow, arterial flow, capillary or arterial distal flow, micro and macro flow, and angiosome mapping as the foundation of a PAD, CLI and/or wound healing evaluation and/or classification system to more effectively assess and communicate the severity and stage of disease states. Optional inputs include established disease scoring and/or classification systems as hereinafter described.

The present invention incorporates angiosome mapping with functional markers and other clinical indices to provide a PAD, CLI and/or wound healing evaluation system. The inclusion of angiosome mapping brings new perspective to the anatomical and functional considerations that inform education, diagnosis, therapeutic management and communication applications.

The invention includes a method and system for assessing the severity and stage of PAD and/or wound healing. The invention includes at least one sensor adapted to measure peripheral vascular conditions of a patient; a lower extremity angiosome knowledge base that provides data on lower extremity angiosomes; and a processing device in operable communication with the sensor and the lower extremity angiosome knowledge base. The processing device outputs a visual representation of at least one of the lower extremity angiosomes included in the knowledge base, the visual representation to guide the placement of the sensor in the mapping of a testing site relative to a target vessel for the skin perfusion pressure measurement. The processing device receives the vascular measurements based on the angiosome mapping and produces data that is indicative of the severity and stage of lower extremity disease. The sensors may include one or more sensors for measuring skin perfusion pressure, tissue CO2, temperature as other sensors known to those of skill in the art. Lower extremity disease includes but is not limited to peripheral arterial disease and wound healing potential.

The invention also includes a method of providing a sensor for measuring peripheral vascular conditions, a knowledge base that provides data on lower extremity angiosome and a processing device in operable communication with the knowledge base. The processing device displays an angiosome map based upon the expected normal underlying arterial architecture. Vascular inputs from sensors, images, or other means are used to assess and interrogate the skin to "inform" the angiosome map by overlaying sensor-acquired information, (referred to herein as sensor fusion). This sensor fusion can then be used to localize disease to an angiosome, assist intervention planning and assess outcomes following intervention. The processing device outputs data that is indicative of the severity and stage of peripheral arterial disease and wound healing potential to produce a new understanding of the angiosome as it has been altered by disease.

The system in accordance with the present invention optionally includes a knowledge base of disease scoring and/or classification systems and a knowledge base for providing information on peripheral arterial disease.

The system in accordance with the present invention optionally includes a display device for displaying the output.

The present invention automates and, therefore, objectifies the method and system of assessing and communicating the severity and stage of peripheral arterial disease and lower extremity wounds using angiosome mapping.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

The present invention is based on the inventors' discovery that the measurement of mechanical factors alone, such as arterial and distal arterial blood flow, does not necessarily objectively assess the severity and stage of peripheral arterial disease and lower extremity wounds. The present invention is also based on the inventors' discovery that there are simple, objective parameters that can be measured within discrete angiosomes and that the paired use of parameter measurement and reporting within discrete angiosomes replaces subjective diagnostic methods.

Thus, the present invention is directed to the measurement of mechanical factors such as arterial and distal arterial blood flow, optionally combined with established disease scoring and/or classification systems, the foregoing integrated into and correlated with angiosome mapping as the foundation of a PAD, CLI and/or wound healing evaluation system to effectively assess the severity and stage of peripheral arterial disease and lower extremity wounds. Optionally, the novel invention can utilize the foregoing in combination with metabolic factors such as the measurement of $pCO_2$.

The methods and devices of the invention measure blood flow in tissue at a relevant local site such as proximal to the wound or peri-wound. Relevance is defined according to the location of the wound within an angiosome. In situations where the ulcer or wound is severe, peri-wound measurements are thus utilized effectively. In general, these measurements are made by placing a blood-flow sensor such as a laser-Doppler sensor or an ultrasound Doppler sensor in an angiosome. If a wound is present, the measurement is made reasonably close to, but not directly in, the wound site and the sensor measures blood flow at the selected site. If a wound is not present, several measurements may be made in various angiosomes. Alternatively, continuous monitoring measurements can be utilized. PVRs are made at several levels as prescribed by standard arterial testing protocols. Optionally, all testing is performed bilaterally for completeness.

SPP measurements are taken to determine whether local blood flow, i.e. capillary perfusion, of a local or regional body site having an ulcer or wound is sufficient to support wound healing. The accurate measurement of this parameter, therefore, is critical to physicians who treat patients suffering from open surface wounds resulting from complications from diabetes, PAD, pressure ulcers, trauma, venous insufficiency, and the like. SPP is also measured when no wound exists as part of the assessment of the effects PAD and CLI have on local or regional tissue perfusion.

Figure 1:
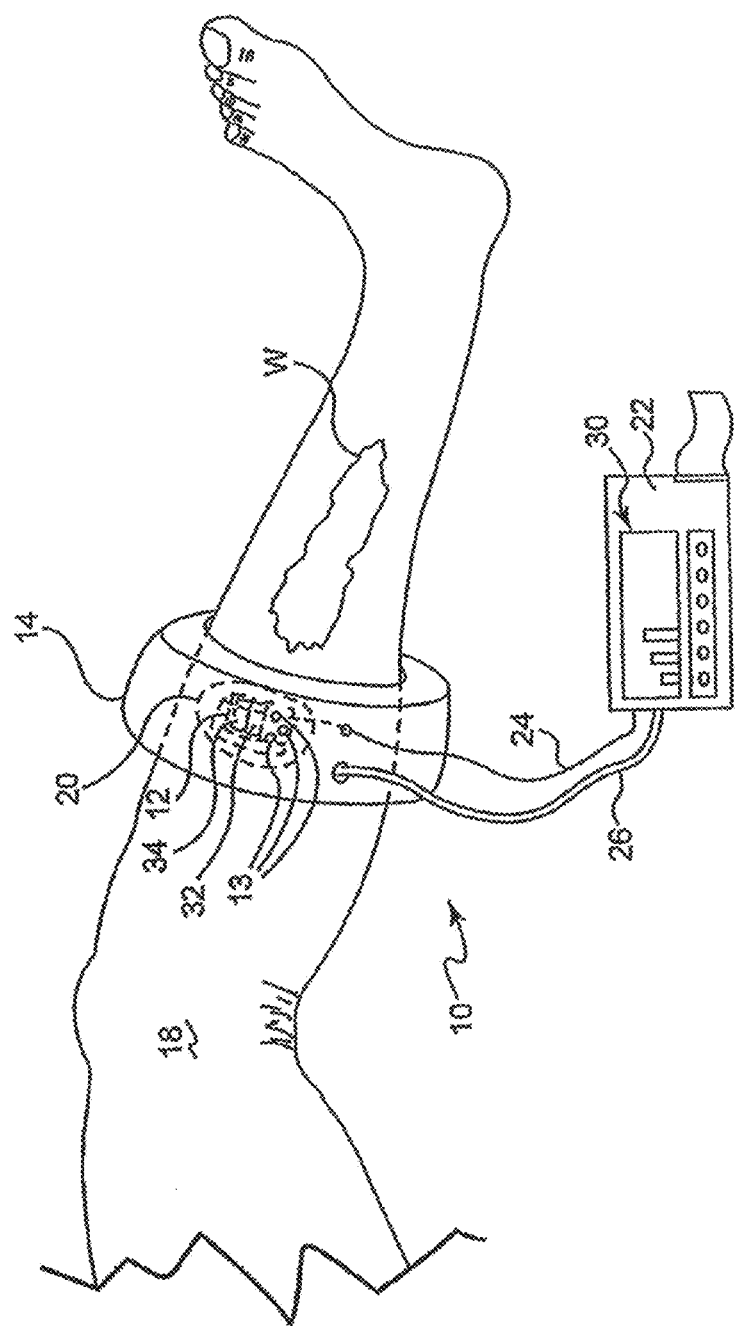
FIG. 1 is a schematic representation of an embodiment of the measurement device in use with a patient in accordance with the present invention in which the pressure cuff and applicable sensors are placed peri-wound.

Referring to FIG. 1, a schematic diagram depicting a representative, but not limiting, perfusion pressure monitoring system 10 is illustrated. The skin perfusion pressure monitoring system 10 broadly includes optical probe or sensor 12, pressure cuff 14, and skin perfusion pressure instrument 22 with display monitor 30. The optical probe 12 is positioned underneath pressure cuff 14 proximate the skin of the patient's limb 18. Alternatively, optical probe 12 may be positioned distal to cuff 14 or inside cuff bladder 14. In an alternative embodiment, cuff 14 may include a transparent window to observe optical probe 12. The skin perfusion pressure instrument inflates the pressure cuff 14 through tube 26. The size of pressure cuff 14 may be varied depending on whether the limb involved is the arm, toe, leg, ankle, etc. but must be capable of sustaining a sufficiently high pressure (above systolic) to temporarily stop tissue blood flow at the site of the optical probe 12 in the observation volume of tissue 20. The observation volume of tissue 20 may be at the same location as the applied pressure, at a location near the applied pressure, or distal from the applied pressure, e.g. where flow is measured on the toe and pressure is applied at the ankle. The skin perfusion instrument 22 is coupled to the optical probe 12 via a fiber optic cable 24, and the pressure cuff 14.

The optical probe 12 monitors microcirculatory flow within the observation volume of tissue 20. Microcirculation detected within the observation volume of tissue 20 is expressed as a percent and displayed on the Y-axis of the perfusion pressure display instrument. The percent value is shown as both a numeric value, typically from 0% to 10% and graphically is shown as a bar graph on the Y-axis of the instrument display 30. The skin perfusion pressure instrument 22 also measures the pressure within the cuff 14 and displays the applied cuff pressure in millimeters of mercury on the X-axis of the display in descending uniform increments.

Optical probe 12 depicted in FIG. 1 includes at least a laser transmitter fiber 32 and at least one receiver photodiode 34. In an alternative embodiment, the laser or photodiode, or both, may be placed in probe 12 without a need for fiber optic elements. In operation, coherent light supplied from a solid state, or other laser device within the perfusion pressure display instrument 22 is conducted to the transmitter fiber 32 that is in contact with the patient's skin through the pressure cuff 14 bladder. Photons emitted from the transmit fiber 32 are scattered by the patient's tissues. A small portion (less than 5%) of the emitted photons is collected by the receiver fiber 34. The spacing between the fibers and the optical apertures of the fibers establish the volume of tissue that is monitored. Typically a single transmitter fiber is used with a pair of receiver fibers. The nominal fiber core diameter is on the order of 50 to 100 microns and is used to establish an observation volume of approximately one to two cubic millimeters.

Notwithstanding, those skilled in the art will recognize that there are many ways to determine the point at which microcirculatory flow returns to a given observation volume. For example, visual observation such as the change in color of the observation site; ultra-sound; optical plethysmography, measurements of increases in temperature; sound, e.g. a microphone for pulsatile flow in the macrocirculation; metabolic indicators such as $pCO_2$ or lactate; and bioimpedance or pulse oximetry or both, each with a pulsatile measurement and a blood volume measurement.

The optical probe includes at least a laser transmitter fiber and at least one receiver photodiode. In an alternative embodiment, the laser or photodiode, or both, may be placed in the optical probe without a need for fiber optic elements. In operation, coherent light supplied from a solid state, or other laser device within the perfusion pressure display instrument is conducted to the transmitter fiber that is in contact with the patient's wound through the pressure cuff bladder. Photons emitted from the transmit fiber are scattered by the patient's tissues. A small portion (less than 5%) of the emitted photons is collected by the receiver fiber. The spacing between the fibers and the optical apertures of the fibers establish the volume of tissue that is monitored. Typically a single transmitter fiber is used with a pair of receiver fibers. The nominal fiber core diameter is on the order of 50 to 100 microns and, when combined with distance to receiving fiber, is used to establish an observation volume of approximately one to two cubic millimeters.

Those skilled in the art will recognize that there are many ways to determine the point at which microcirculatory flow returns to a given observation volume. For example, visual observation such as the change in color of the observation site; ultra-sound; optical plethysmography, measurements of increases in temperature; sound, e.g. a microphone for pulsatile flow in the macrocirculation; metabolic indicators such as PCO2 or lactate; and bioimpedance or pulse oximetry or both, each with a pulsatile measurement and a blood volume measurement.

Some back-scattered photons are frequency shifted by moving cells present in the microcirculation. The collected photons are collected by the capillary vitality instrument via a cable where they impinge on a photodiode. Thus, photons are impinging on the photodiode as a result of scattering off moving and stationary cells. The photodiode voltage contains both frequency and power information. The Doppler shifted frequency is related to cell velocity while the spectral power information is related to the volume of moving cells at that given frequency. The DC signal component results from the total number of photons received by the receive fiber. The AC signal component results from the mixing of frequency shifted photons with photons from stationary structures. If the number of moving cells present within the observation volume increases then the magnitude of the AC component will increase while the DC offset will remain nearly constant. The AC component increases because more returned photons undergo a Doppler shift. The DC component remains nearly constant because the total number of photons scattered by collisions with stationary cells within the measurement volume is reduced only slightly by moving cells. Therefore, the perfusion measurement is proportional to the ratio of the AC signal to the DC signal, which is an indication of the volume of moving cells in the observation volume of tissue. This type of measurement is commonly computed with both analog and digital signal processing. For example, it is common to convert the AC signal to an RMS equivalent through analog processing. It is these values that are presented to the A/D converter. The microprocessor then may square these digitized values prior to forming the ratio. The ratio value may be scaled by an empirically derived scaling factor that depends on the gain distribution throughout the signal processing paths.

SPP measurements as described above measure the microcirculation of the patient in the area of interest. It is a distal arterial test and an indicator of wound healing potential and disease severity. Skin perfusion pressure measures, in millimeters of mercury, the pressure at which blood flow first returns to the capillaries following controlled occlusive release.

The inventors of the present invention have also discovered that the measurement of skin perfusion pressure can be further refined by measuring air plethysmography. Air plethysmography (APG) is a technique that allows the measurement of limb volume changes with different maneuvers. APG utilizes a cuff that is placed around the leg, a calibratable pressure transducer, and in the case of the present invention an instrument that provides a visual display. Parameters derived from performing various APG measurements with positional changes include the venous filling index, which quantifies venous reflux, the ejection fraction, which correlates with calf muscle pump function, and the residual volume fraction, which correlates with ambulatory calf venous pressure. Venous occlusion techniques allow the measurement of arterial flow into the limb and the venous outflow fraction, which can be used to evaluate venous obstruction. Differentiation of pathology in the deep venous system from that in the superficial venous system is possible.

Alternatively, the inventive instrument may utilize optical plethysmography with light absorbance technology to reproduce waveforms produced by pulsating blood. Typically non-visible infrared light is emitted into the skin. More or less light is absorbed, depending on the blood volume in the skin. The backscattered light corresponds with the variation in blood volume. Blood volume changes are then determined by measuring the reflected light and using the optical properties of tissue and blood. The optical plethysmography measurement may be obtained by volume displacement plethysmography or by electrical impedance plethysmography as those skilled in the art can appreciate. Typically the tissue under investigation is bathed with light of a suitable wavelength and the resultant scattered light is measured with a silicon photodiode. The received signal is assumed to be a measure of volume changes due to localized blood flow.

Optical or air plethysmography measurements may be used in conjunction with the skin perfusion pressure measurements disclosed herein.

The foregoing measurements have been named pulse volume recordings and measure the macrocirculation of the patient. Alone or in combination SPP and PVR may provide an assessment of arterial circulation in the area of interest for diagnostic consideration.

Thus, laser-Doppler, ultrasound-Doppler, and other blood-flow measurement instruments that measure skin perfusion pressure used in conjunction with air or optical plethysmography can be used to assess micro-circulatory and macro-circulatory health.

Figure 7:
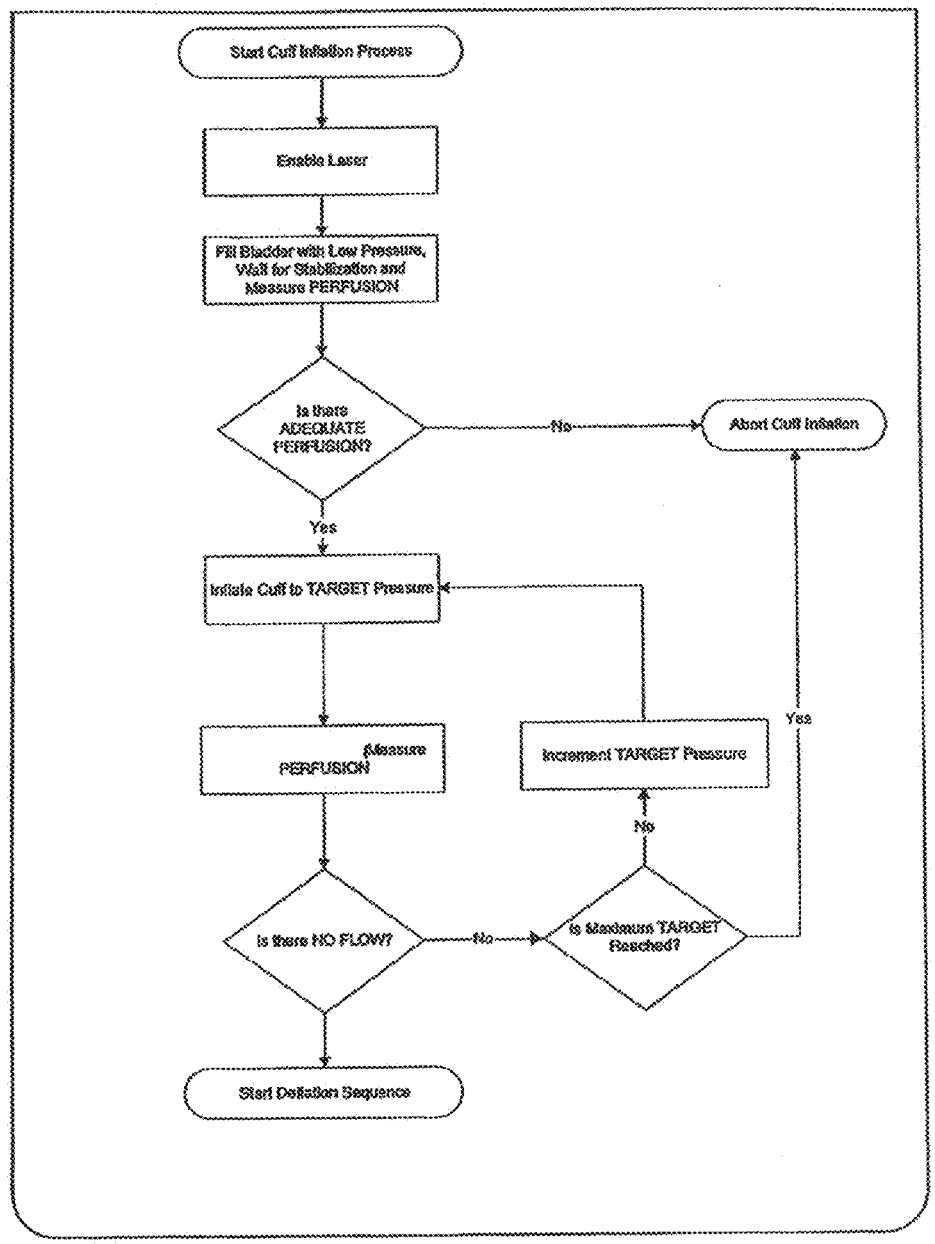
FIG. 7 is a flowchart representing the operation of a perfusion pressure monitor with respect to inflation of the system for assessing severity and stage of peripheral arterial disease and wound healing potential in accordance with the invention.

Referring now to FIGS. 1 and 7, the cuff inflation sequence the commences the recording of a skin perfusion measurement is illustrated. The skin perfusion instrument 22 commences the cuff inflation process and the laser in optical probe 12 is enabled. The cuff 14 bladder is initially filled with a low pressure, such as 5 to 10 mmHg, to ensure that the sensing probe is in contact with the patient's skin so that adequate perfusion can be detected and measured. If adequate perfusion cannot be measured, cuff inflation is aborted and the test does not proceed. If adequate perfusion can be measured, the pressure cuff 14 is inflated to the target pressure, near or at systolic and perfusion is measured. If "no flow" is not achieved at this target pressure and the maximum target pressure has not been reached, pressure is increased incrementally (e.g. 40 mmHg increments) and the "no flow" criteria is tested again. If the maximum target pressure has been reached, and the "no flow" criterion still has not been met, cuff inflation is aborted and the test discontinued.

Figure 8:
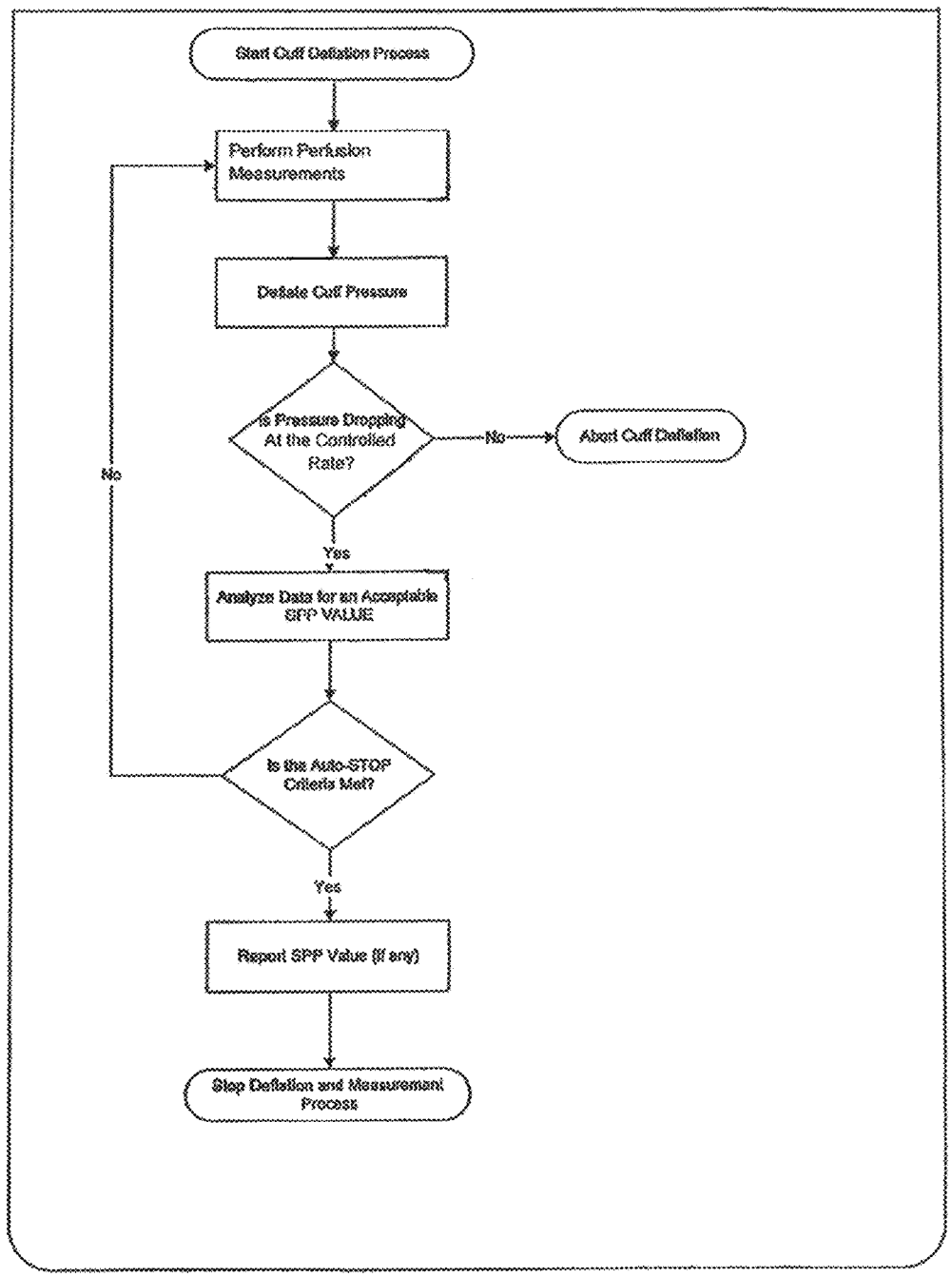
FIG. 8 is a flowchart representing the operation of the perfusion pressure monitor with respect to deflation of the system for assessing severity and stage of peripheral arterial disease and wound healing potential in accordance with the invention.

FIG. 8 depicts the cuff deflation sequence. As noted above, if the skin perfusion pressure instrument recognizes a "no flow" signal, cuff pressure starts to automatically deflate at a controlled rate. A controlled rate of deflation provides reproducibility from measurement to measurement on the same patient and between patients. If the pressure is not dropping at the controlled rate, which may be caused by severe patient movement, cuff deflation is aborted and the test discontinued. If the pressure is dropping at the controlled rate, $P_0$ is analyzed for an SPP value. If all conditions for an SPP value are met, e.g. those discussed below, an SPP value is reported. If the conditions are not met, the test continues for a specified time period after which perfusion measurements are displayed for the physician to interpret but an SPP value is not reported for that test. The physician can then use the displayed perfusion data along with any other information that is available to her to determine whether another test should be conducted or if based on her expertise, she can determine an appropriate SPP value.

Figure 9A:
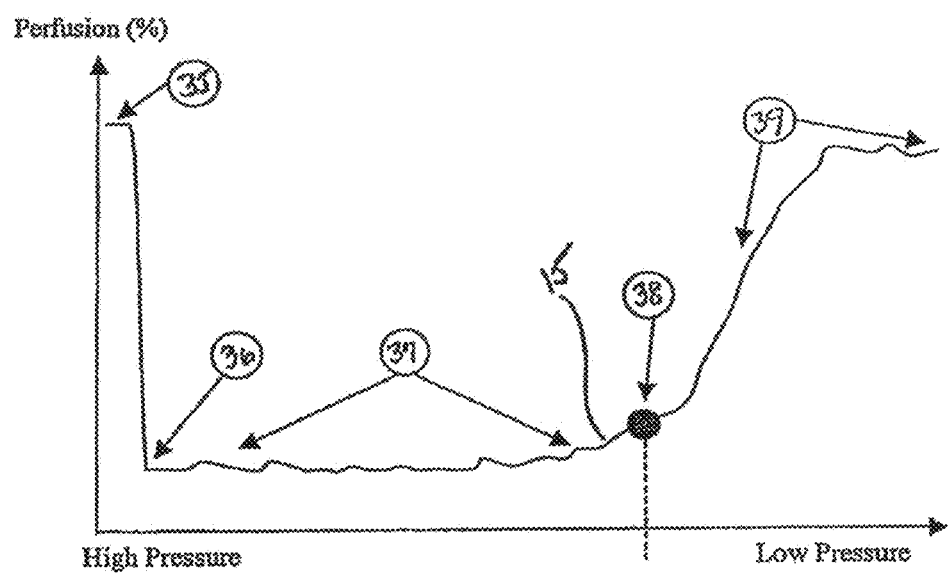
FIG. 9A is a schematic diagram illustrating the pressure line output display of the skin perfusion pressure monitor of the system for assessing severity and stage of peripheral arterial disease and wound healing potential in accordance with the present invention.
Figure 9B:
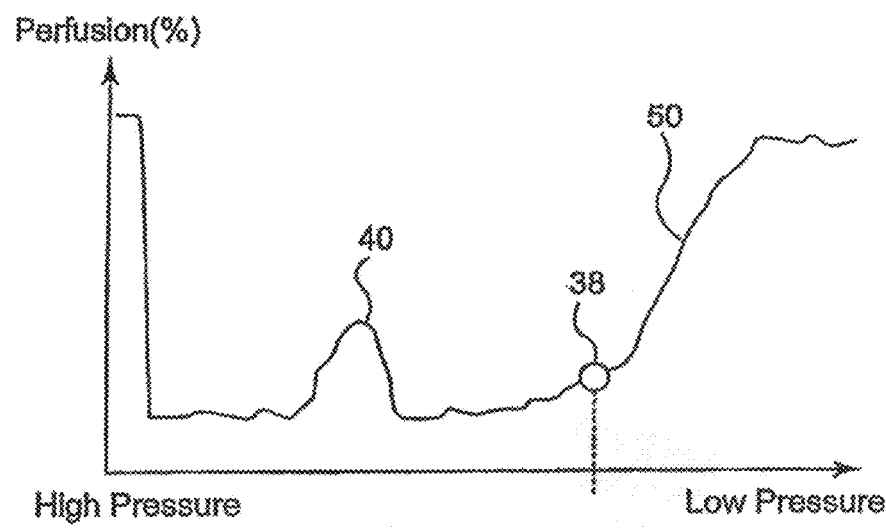
FIG. 9B is a schematic diagram illustrating the pressure line output display of the skin perfusion pressure monitoring of the system for assessing severity and stage of peripheral arterial disease and wound healing potential in accordance with the present invention with a spike indicating motion artifact.
Figure 9C:
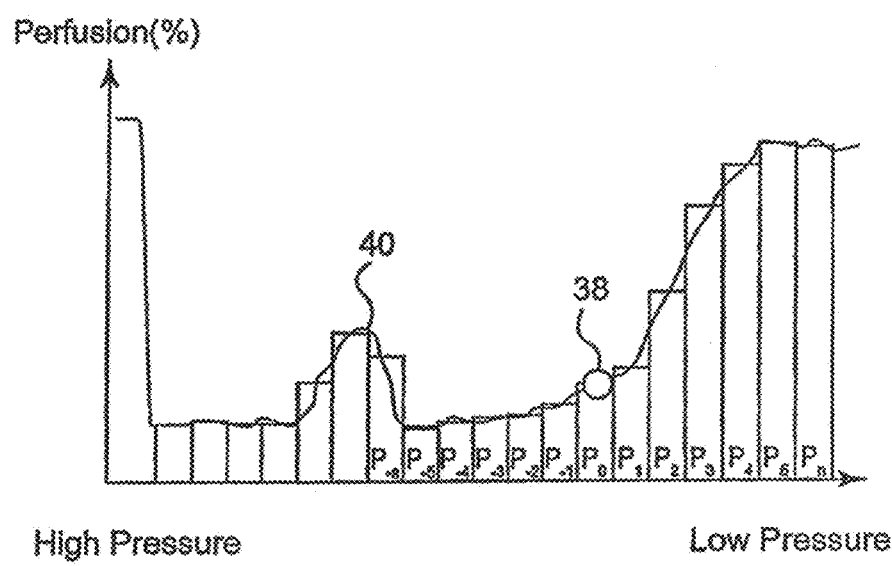
FIG. 9C is a schematic diagram illustrating the pressure line output display of the skin perfusion pressure monitoring of the system for assessing severity and stage of peripheral arterial disease and wound healing potential in accordance with the present invention with a spike indicating motion artifact, bars, and a true reading of surface perfusion pressure.

FIGS. 9A-C illustrate different stages of output data as depicted on the display monitor. Referring to FIG. 9A data being recorded during the testing procedure is displayed. Moving line 15 rises as pressure decreases. As can be seen, points representing adequate perfusion 35, no flow 36, baseline flow 37, SPP value 38, and the return of normal microcirculation 39 are depicted. FIG. 9B illustrates the same pressure line that rises as pressure decreases but now displays motion artifact 40. As illustrated, the skin perfusion pressure monitoring system in accordance with the present invention rejects motion artifact as not being a perfusion measurement and the test continues as seen by continuing line 15. Referring to FIG. 9C, the skin perfusion pressure monitor in accordance with the present invention analyzes numerous different criteria for detecting and rejecting motion artifact in qualifying $P.sub.0$ for a SPP value. If $P.sub.0$ has been qualified as an SPP value, a bar graph is overlaid on line 15, as best seen in FIG. 9C, and the SPP value 38 is recorded. As those skilled in the art can appreciate, any graphical representation can be used to depict the perfusion measurement data set. The skin perfusion pressure monitoring system 10 considers unique criteria in qualifying $P.sub.0$ as an SPP value and in assessing whether motion artifact is present. Those skilled in the art can appreciate that many or few criteria may be considered. In addition, other criteria can be used other than those described below. For example, linear regression, slope intercept, differentiation, weighted average, and other known mathematical models may be used in addition to or in lieu of the criteria listed below. Whether the number of criteria considered is few or many, all criteria will be used to reject unwanted noise, environmental influences, or motion in combination with the qualification of a pressure at which microcirculatory flow returns to the observation or measurement volume.

Initially as a first criterion, $P.sub.0$ must be within a valid range for the system to qualify an SPP value. If $P.sub.0$ is not within a valid range, for example from approximately 1 mmHg to approximately 150 mmHg, the system will not indicate that a particular $P.sub.0$ is an SPP value.

Another criterion is whether the perfusion increase is large enough relative to the measurement. If the perfusion increase is not large enough an SPP value will not be qualified. In interpreting "step size" (i.e. perfusion increase large enough from the prior measurement) the instrument uses a perfusion sensitive tolerance that progressively adjusts sensitivity thresholds as perfusion returns. This allows the system to qualify SPP values over a wide dynamic range while being less sensitive to motion transients. For example, if perfusion is very low then the instrument allows for the detection and rejection of motion artifact due to its perfusion sensitive tolerance. If the perfusion measurement is greater than 0.20% (i.e. high perfusion measurement) and the applied cuff pressure is less than 100 mmHg a perfusion increase of from 10% to 50% and preferably 25% relative to the prior measurement, is necessary. If the perfusion measurement is greater than 0.20% (i.e. high perfusion measurement) and the applied cuff pressure is greater than or equal to 100 mmHg a perfusion increase of from 20% to about 80%, and preferably 40%, relative to prior measurement is necessary. If the perfusion measurement is between 0.15 to 0.20% (i.e. medium perfusion measurement) and the applied cuff pressure is any valid pressure a perfusion increase of from 25% to 100%, and preferably 50%, relative to the prior perfusion measurement is necessary. If the perfusion measurement is less than 0.15% (i.e. low perfusion measurement) and the applied cuff pressure is any valid pressure a perfusion increase of from 50% to 200%, and preferably 100%, relative to the prior perfusion measurement is necessary.

Those skilled in the art will recognize that the foregoing criterion does not need to be limited to high, medium and low perfusion measurements or a few isolated points for applied cuff pressure, i.e. above and below 100 mmHg. These may be expressed as a continuous function of perfusion measurements or applied cuff pressure, or both.

Another criterion is whether the perfusion measurement under evaluation, i.e. $P.sub.0$, is large enough, i.e. whether flow is above baseline. The perfusion should be preferably from between 0.05 to 0.2% and more preferably at least 0.10% at point $P.sub.0$ or no skin perfusion pressure will be recorded.

Another criterion determines whether the "next steps," i.e. those following point $P.sub.0$, are increasing or decreasing. Next steps must not be decreasing as this is not characteristic of a typical signature for returning microcirculatory flow to an observation volume with decreasing pressure. This fourth criterion focuses on the duration of increasing perfusion change. As microcirculation flow returns it produces a perfusion signal that increases and holds in a signature pattern. Motion artifact produces a perfusion signal that has more oscillatory content, thereby having greater tendencies to decrease.

When applied cuff pressure is low, i.e. preferably from about 0 to 20 mmHg and more preferably less than 15 mmHg, the number of next steps analyzed in determining whether next steps are increasing or decreasing is one. When the applied cuff pressure is in a medium range, for example from about 10 to 50 mmHg and more preferably from about 15 to about 20 mmHG, the number of next steps analyzed in determining whether next steps are increasing or decreasing is two. When applied cuff pressure is high, for example from about 40 to 120 mmHg and preferably greater than 50 mmHg but less than 100 mmHg, the number of next steps analyzed in determining whether next steps are increasing or decreasing is three. When pressure is very high, preferably from 80 to 150 mmHg, and most preferably greater than 100 mmHg, the number of next steps analyzed in determining whether next steps are increasing or decreasing is five. The higher the number of next steps being analyzed, i.e. N, the more confidence that the system has qualified an SPP value.

Another criterion for detecting and rejecting motion artifact is the profile of perfusion change. Microcirculation produces a perfusion signal that increases step-wise while motion produces a perfusion signal that has more oscillatory content. Changes that do not follow a perfusion return signature are ignored. Referring again to Table II, the perfusion change profile criterion for detecting and rejecting motion artifact is whether the specified number of steps following $P.sub.1$ are at least at or above the perfusion value for $P.sub.1$. These steps must not be decreasing. In other words, $P.sub.2$ to $P.sub.N$ must all be greater than $P.sub.1$. This criterion is especially effective in rejecting motion, as those signals are not long-lived.

If all criteria are met the skin perfusion pressure system will qualify $P.sub.0$ as the SPP value 38.

The instrument in accordance with the present invention may utilize an entirely software embodiment or an embodiment containing both hardware and software elements. In one embodiment, the invention is implemented in software, which includes but is not limited to firmware, resident software, microcode, etc. The invention can also take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem, wireless devices and Ethernet cards are just a few of the currently available types of network adapters.

Figure 2:
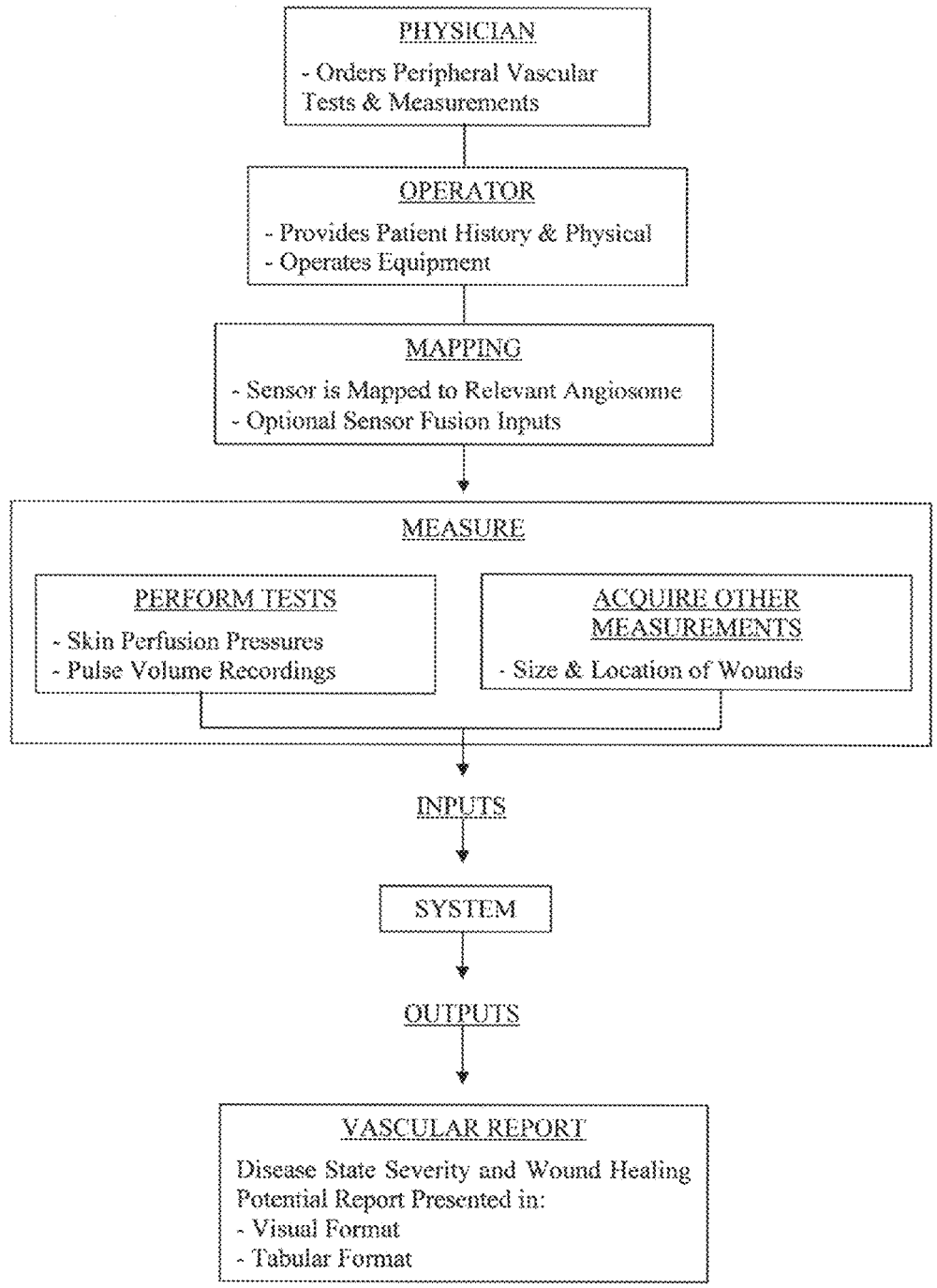
FIG. 2 depicts a flow chart that represents the typical flow of the test procedure.
Figure 3:
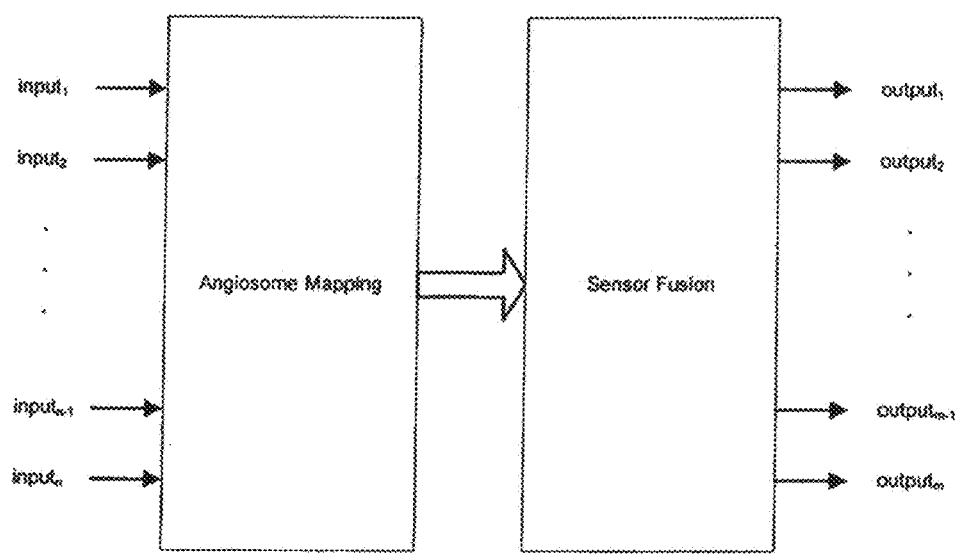
FIG. 3 is a flow chart schematically depicting inputs into the angiosome map, sensor fusion and output data.

Referring now to FIGS. 2 and 3, history and physical exam (H&P) parameters are provided by an operator. Alternatively, H&P parameters can be obtained from an electronic medical record. Physical examinations for peripheral vascular conditions commonly assess: indications of trauma, muscle wasting, muscle asymmetry, temperature, edema (swelling), erythema (redness), ulcers, shiny skin, capillary refill, and absence of hair.

An angiosome map is displayed by the system. A skin perfusion measurement sensor is overlaid on the angiosome map and the sensor is mapped to a relevant angiosome where testing is to be done. Tests and other measured parameters for assessment of peripheral vascular conditions for assessment by the system may include: SPP, PVR, transcutaneous oxygen monitoring (TCOM), ankle brachial index (ABI), tissue CO2, temperature, spectral imaging, and hyperspectral imaging.

The instrument utilizes all available information and measured parameters, which are referred to as inputs. Each input supports assessment of a disease state or is correlative or otherwise associated with a disease state. As an example, measures of SPP correlate with PAD and the likelihood of wound healing. Similarly, PVR waveforms are indicative of large vessel disease. Inputs would also be associated with a single angiosome or multiple angiosomes, as applicable. Inputs can also be associated with a specific location within an angiosome or specific site on a limb.

Inputs can be highly varied. Inputs can consist of disparate measures, for example SPP and PVR. Inputs can consist of multiple measures within a single angiosome, for example several SPP measures within a single angiosome. Inputs can even consist of measures or information obtained at different points in time.

Angiosome mapping considers, for each input, the angiosome where the input was acquired, left or right limb, and may also consider the site within the angiosome. Inputs can be combined by utilizing any of several known sensor fusion methods. Examples of sensor fusion methods include Kalman filter, Bayesian network, and Dempster-Shafer theory. Inputs can be weighted based on confidence, reliability, or how recent input was obtained. Other methods for sensor fusion and weighting are known to those skilled in the art.

The output can be provided in one or more of several methods. Output can be provided in a visual presentation associated with the angiosome model where a disease state metric can be displayed in a color coded or otherwise shaded manner specific to each angiosome. Output can be provided in a tabular manner. Output can be provided to an electronic medical record or medical information system.

Figure 4:
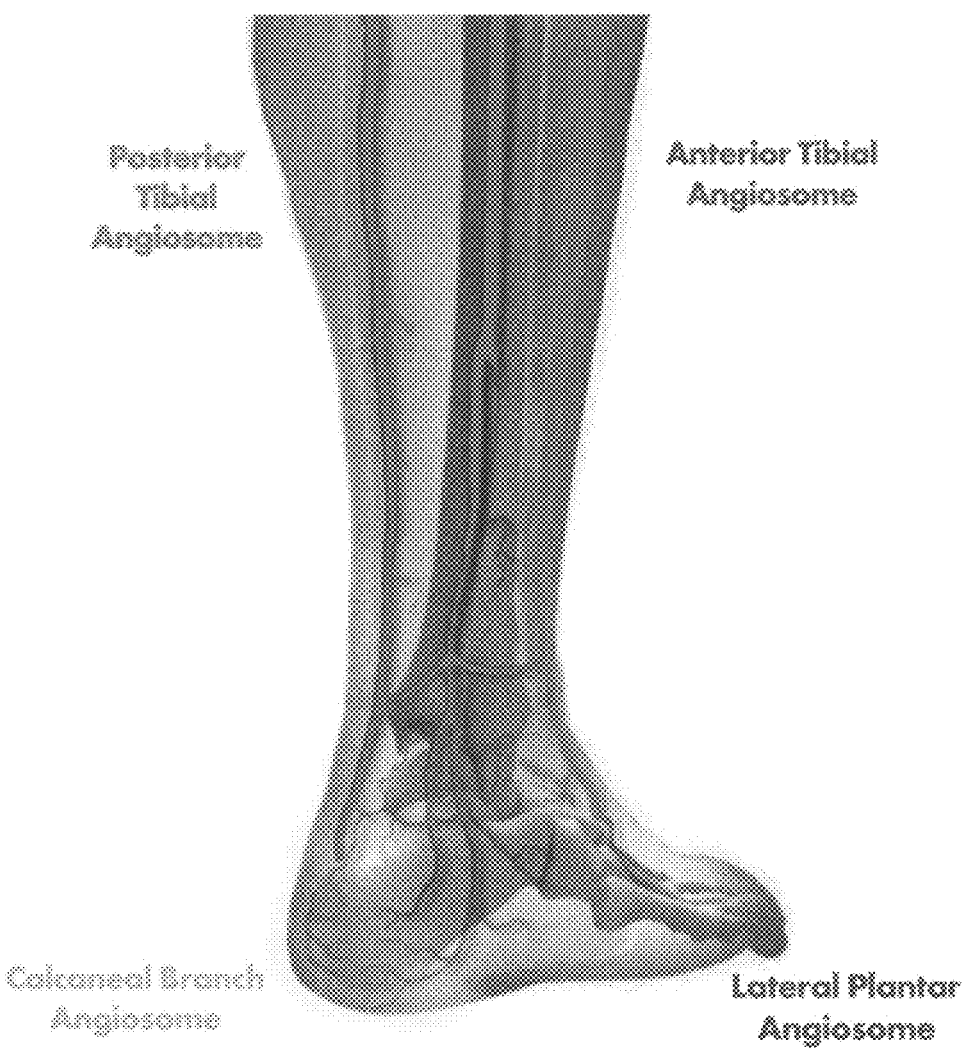
FIG. 4 is an illustrative three-dimensional angiosome map prior to the inputting of data in accordance with the present invention depicting the posterior tibial, anterior tibial, calcaneal branch and lateral plantar angiosomes.
Figure 5:
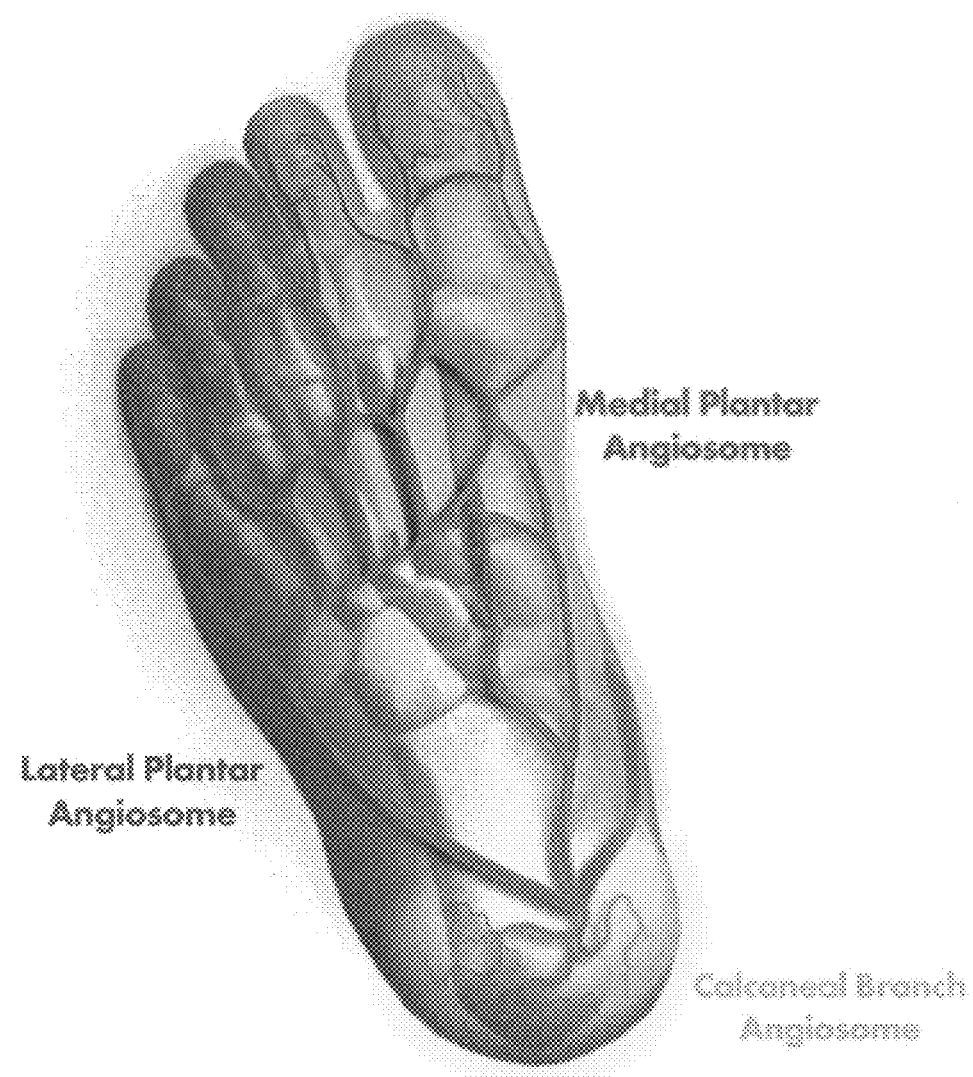
FIG. 5 is a further illustration of an angiosome map prior to the inputting of data in accordance with the present invention depicting the lateral plantar, medial plantar and calcaneal branch angiosomes.
Figure 6:
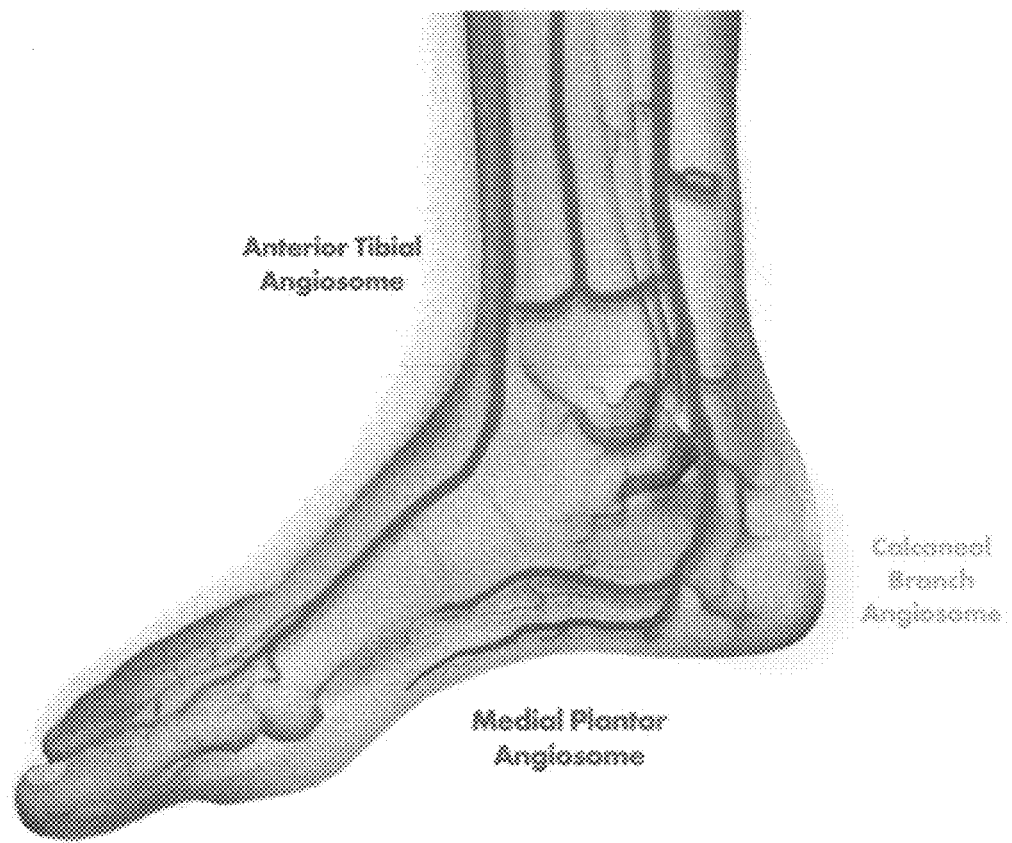
FIG. 6 is a further illustration of an angiosome map prior to the inputting of data in accordance with the present invention depicting the anterior tibial, medial plantar and calcaneal branch angiosomes.

Referring now to FIGS. 4, 5, and 6 the instrument in accordance with the present invention combines anatomical structures (skin, vascular, and skeletal) into computer-generated three dimensional angiosome map that objectifies the stage and severity of PAD and lower extremity wounds. FIGS. 4, 5 and 6 depict exemplary angiosome regions prior to the inputting of data. The instrument in accordance with the present invention provides a computer-generated novel and unobvious three-dimensional anatomical model. This three-dimensional model contains skeletal structure, vascular structure, and skin tissue blocks defined by particular vascular structure. In addition, a unique aspect of this invention allows for two-dimensional print out of the computer generated three-dimensional model that contains skeletal, vascular and angiosome structures. The angiosome map allows the physician to view all foot and leg angiosomes even if located beneath the skin surface, as will hereinafter be described. Placement of the laser Doppler and other sensors in an angiosome of key interest provides the most accurate readings of blood flow and other parameters, as well as reliable and reproducible results.

The present invention combines all components integral to utilizing angiosomes to assess the severity and stage of PAD both in terms of etiology, location and severity to support optimal diagnosis of PAD and healing of wounds in ischemic limbs and the like.

The instrument in accordance with the present invention generates an angiosome map that distinguishes between vascular systems, in other words arterial and venous structures and other anatomical information such as the nervous system.

Other attributes of the angiosome map include various methods of color-coding, highlighting, ghosting or other means to facilitate discrimination between structures and allows for customization and scaling for patient-specific attributes such as size, weight, age and gender.

The angiosome map in accordance with the present invention may represent various disease states. One frequently seen condition that could be represented is arterial constriction/obstruction and secondary arterial development such as the presence of collaterals resultant of chronic obstructions and small vessel disease process.

The angiosome map in accordance with the invention can optionally be used as the foundation of a PAD, CLI and/or wound healing scoring system for incorporation into established classification systems such as the Trans Atlantic Scoring Classification (TASC), Rutherford Categorization System, Fontaine, University of Texas Diabetic Wound Classification System and the Wagner Scale for wound categorization.

The angiosome map in accordance with the invention can be designed to be customized to a patient's position during evaluation as well as stressors that are employed during testing. Examples of stressors include but are not limited to limb elevation, changes in externally applied pressure and temperature.

The angiosome map can be integrated with input obtained from a patient. The input may be either directly measured input or software-communicated input. An example of direct measurement input is one wherein perfusion within one or more of the six angiosomes is measured for input. An example of software-communicated input is one in which the new model can obtain three dimensional magnetic resonance imaging scans of a patient's vascular structure, overlay the patient information with model information, and present this information back to the user in a manner that includes angiosomes. Input can consist of history and physical exam parameters such as age, height weight, temperature, edema, erythema; skin perfusion pressure measurements; pulse volume recording; transcutaneous oxygen monitoring; ankle brachial index; tissue CO2; and other such parameters.

The angiosome map in accordance with the present invention can also optionally be integrated with existing disease scoring and/or classification systems and wound healing assessment scoring systems. In one example, a medical device in which a user places a sensor on the skin for measurement of parameters measurable on and/or through the skin. These include but are not limited to images (photographic, thermographic, hyperspectral), electrical signals, blood and blood component flow and the related attributes of blood and blood component flow such as temperature and metabolites (oxygen, hemoglobin, carbon dioxide) can benefit if the user can be presented, via the invention, with a depiction of vascular sources supplying the skin tissue. In one embodiment, the user could maneuver a model by means of a computer interface to analyze the vascular structure supporting the area of skin being measured and also to indicate the location where a sensor is placed.

Treatment or surgical medical devices can be improved by this invention. In one example, a medical device in which a user treats a wound can benefit if the user can be presented with the underlying vascular structure and its relationship with the area of skin in which the wound resides.

While the underlying angiosome model is inherently a computer-generated, three-dimensional model, a two-dimensional format can be generated and utilized when discussing diagnoses with patients and other physicians and health care workers. Two dimensional presentations of three dimensional structures could also be provided on a computer display. Because the underlying model is three dimensional, the viewpoint could be controlled by a user such as being rotated or even stressed in some way. Also, a user could be allowed to control several aspects of the presentation. For example, a user could control whether certain underlying structures are displayed, to what extent certain underlying structures are highlighted or enhanced, or the user could enable color coding of certain features such as having different angiosome presented in different colors.

The angiosome map in accordance with the present invention provides more accurate information to assess stage and severity of PAD because multiple anatomical features can be represented in one model versus having to reference two different models (illustration and photos) for a complete picture. Examples of multiple anatomical features that might be included in a three dimensional angiosome model are skin, vascular structure, and skeletal structure. The invention allows the user to customize a view selection e.g. allowing a user to view an angiosome structure from the same viewpoint in which they are examining a subject or patient. It further permits an illustrative venue for the user to gain greater understanding of the physiological development of disease processes and the effect of these processes on a specific condition (e.g., arterial obstruction in limb leading to either an ischemic condition and non-wound healing, or chronic arterial obstruction that over time is mitigated by development of collateral flow).

Based upon the degree of PAD, ranging from asymptomatic to ischemic ulceration, gangrene, and tissue loss, two major classifications of PAD have been developed. The Fontaine classification uses four stages. Fontaine I represents those who are asymptomatic; IIa and IIb are mild and moderate-severe pain are Fontaine Ills; and ulcerations and gangrene represent Fontaine IV. A similar classification scheme has been developed by Rutherford. The Rutherford classification has four grades, 0-III, and six categories, with grade I having three categories. This classification system is similar to Fontaine's, except claudicants have four categories and tissue loss is subdivided into two categories, minor and major.

The TransAtlantic Inter-Society Consensus (TASC), a diagnostic and therapeutic guideline, combined the Fontaine classification with the Rutherford classification as the criteria in 2000, re-defining degree I of class I as asymptomatic. The Rutherford Classification is the currently recommended standard describing the clinical assessment of patients with PAD. Accordingly, patients with CLI fall into categories 4-6, designated by ischemic rest pain, and minor and major tissue loss, respectively. Foot pain at rest—generally referred to as ischemic rest pain—is considered a milder form, whereas any tissue loss represents a more advanced state of CLI. Categories 0-3 are assigned to asymptomatic patients and those with mild, moderate, and severe Intermittent Claudication. The wound classification systems rely on size, shape and depth of ulceration and include infection and PAD in order to better predict outcome.

The angiosome scoring system in accordance with the present invention replaces subjective assessments with objectively measured data within established classification and scoring systems. The new system obtains knowledge of angiosome site for input data and includes measurements of SPP. One or several angiosomes may be included, dependent on available inputs. Input parameters include skin perfusion pressures because understanding of microcirculatory health is vital to evaluating disease state. Input parameters may include additional parameters such as microcirculatory measures, macrocirculatory measures, metabolic measures, and patient history and physical information.

The present invention also provides the novel method of using the foregoing measurements in conjunction with angiosome mapping to detect and quantify blood flow in angiosome regions that feed tissue that is susceptible to low blood to assess severity and stage of PAD and lower extremity wounds in a patient. These measurements may be used in conjunction with each other and additionally in conjunction with measurements of metabolic factors including pH, $pCO_2$, NADH and $SaO_2$. Measurement of metabolic factors may be taken in the wound when for example the sensors are integrated into the pressure cuff, as illustrated in FIG. 1. Alternatively, and in accordance with physician preference, the metabolic measurement sensors 13 may be utilized peri-wound while the blood flow and pressure sensors are placed in the wound W. Furthermore, measurements using blood flow and pressure sensors may also be taken peri-wound in conjunction with measurements taken by the metabolic sensors 13 as described hereinafter.

Preferably, the blood flow sensor in accordance with the present invention may be positioned in the wound or peri-wound, preferably with the sensor lying immediately above or at the surface of the wound. To minimize patient discomfort, a patch may be placed over the wound with the blood flow sensor placed in or on top of the patch. Alternatively the patch may be a sterile, single use cover that is integrated into the system in accordance with the present invention. If the patch is used in conjunction with the measurement of metabolic parameters as hereinafter described, the patch must be permeable in order to accurately measure tissue gases. The blood flow sensor may also be placed adjacent the surface of the wound that will otherwise minimize discomfort to the patient.

The blood-flow sensor lies in the wound or adjacent the surface peri-wound, in order that it effectively measures blood flow in the tissue. Placement of a blood-flow sensor adjacent the tissue's surface provides a very good quantification of local and/or regional perfusion at all times.

The blood-flow sensor used in the methods and devices of the invention may be any single or arrayed blood-flow sensor suitable for detection of blood flow in the manner described herein, such as laser-Doppler blood-flow sensors, ultrasound-Doppler blood-flow sensors, imaging sensors and so forth. For example, the preferred blood-flow sensor is a laser-Doppler blood-flow sensor.

The blood flow measurement taken with the blood-flow sensor placed against the tissue's surface may be used in conjunction with the SPP index and/or the optical plethysmography index. In order to assess perfusion failure in a patient with this embodiment, one first determines the expected range of measurements for subjects of similar age and health status as the patient as normal measurements of skin perfusion pressure and optical plethysmography may vary with the age of the subject. For a healthy patient, these two indices will be close to one. The blood flow in the wound of the patient, or peri-wound, is determined. Next, the skin perfusion pressure and/or the optical plethysmography measurement is taken. Each of these values are compared with the expected value for a normal subject. In addition, the rate-of-change of the patient's blood flow is measured over time with these measurements. Rising values of blood flow, and an SPP index and an air plethysmography index close to one may tend to indicate recovery but the measurement of PCO2 and factors in conjunction with these measurements is critical to an accurate assessment of stage of PAD and/or wound severity.

In addition, as there are many co-morbid factors, e.g. diabetes, that may affect an accurate measurement of blood flow, the use of blood flow measurements in conjunction with the SPP index and the air plethysmography index allows the physician to more accurately monitor capillary vitality and recovery. These measurements may also be used in conjunction with each other and additionally in conjunction with measurements of pH, PCO2, and SaO2 as hereinafter described.

Additional inputs into the instrument in accordance with the present invention, as previously described, may be made. The new system tabulates and/or visually presents disease stage as a function of angiosome resultant from analysis of input parameters. The existing classification and scoring systems will be updated with this tabulated and/or visual quantified perfusion information obtained from specified angiosomes.

While the invention has been described with reference to the specific embodiments thereof, those skilled in the art will be able to make various modifications to the described embodiments of the invention without departing from the true spirit and scope of the invention. The terms and descriptions used herein are set forth by way of illustration only and are not meant as limitations. Those skilled in the art will recognize that these and other variations are possible within the spirit and scope of the invention.

What is claimed is:

1. A system for assessing severity and stage of lower extremity disease comprising:
   at least one sensor that measures peripheral vascular conditions of a patient;
   a knowledge base that provides data on a plurality of lower extremity angiosomes;
   a processing device in operable communication with said at least one sensor and said knowledge base, said processing device configured to (a) output a visual representation of at least one of said plurality of lower extremity angiosomes, said visual representation to guide the placement of said sensor in angiosome mapping of a testing site relative to a target vessel in an angiosome; (b) receive a peripheral vascular measurement based on said angiosome mapping; and (c) cross reference said peripheral vascular measurement with said knowledge base to generate a cross referenced data result indicative of a severity and stage of lower extremity disease,
   wherein said processing device outputs data that is indicative of said severity and stage of lower extremity disease based on said angiosome mapping based on said cross referenced data result.

2. The system of claim 1 further comprising a knowledge base of disease scoring and/or classification systems and a knowledge base of peripheral arterial disease and lower extremity wounds, wherein said processing device is further configured to cross reference said peripheral vascular measurement with said knowledge base of disease scoring and/or classification systems and said knowledge base of peripheral arterial disease and lower extremity wounds to generate a combined cross referenced data result indicative of the severity and stage of lower extremity disease and further wherein said processing device outputs data that indicative of the severity and stage of lower extremity disease based on said combined cross referenced data result.

3. The system of claim 1 further comprising at least one metabolic sensor for measuring at least one metabolic condition of the patient, wherein said processing device is arranged to receive inputs from said at least one metabolic sensor.

4. The system of claim 1 further comprising at least one skin perfusion sensor for measuring skin perfusion.

5. The system of claim 4 further comprising at least one metabolic sensor for measuring at least one metabolic condition of the patient, wherein said processing device is arranged to receive inputs from said at least one metabolic sensor.

6. The system of claim 4 further comprising a knowledge base of disease scoring and/or classification systems and a knowledge base of peripheral arterial disease and lower extremity wounds, wherein said processing device is further configured to cross reference a skin perfusion pressure value with said knowledge base of disease scoring and/or classification systems and said knowledge base of peripheral arterial disease and lower extremity wounds to generate a combined cross referenced data result indicative of the severity and stage of lower extremity disease and further wherein said processing device outputs data that is indicative of the severity and stage of peripheral arterial disease and wound healing potential based on said combined cross referenced data result.

7. The system of claim 1 wherein said peripheral vascular measurements is selected from skin perfusion pressure, pulse volume recordings, transcutaneous oxygen monitoring, ankle brachial index, tissue CO2, temperature, spectral imaging and hyperspectral imaging.

8. The system of claim 1 further comprising:
an inflatable cuff, wherein said at least one sensor is a skin perfusion measurement sensor in communication with the cuff;
a pressure sensor in communication with the cuff for reading pressure levels in the cuff;
a pressure instrument in fluid communication with the cuff for inflation and deflation thereof, the pressure instrument comprising:
a source of pressurized air; and
a conduit connected to the source of pressurized air and the cuff, thereby placing the source of pressurized air in fluid communication with the cuff, wherein said processing device is operably coupled to said pressure instrument and capable of controlling pressurized airflow to and from the cuff, and further wherein said processing device is arranged to receive inputs from said skin perfusion measurement sensor and said pressure sensor;
a computer program executable by the processing device such that when executed, the computer program causes the processing device to:
initiate an automatic inflation sequence resulting in a no flow condition; initiate an automatic deflation sequence;
automatically qualify a perfusion measurement as a skin perfusion pressure value upon all conditions of a set of predetermined conditions being met during the deflation sequence,
wherein said processing device receives said skin perfusion pressure value based on said angiosome mapping, and cross references said skin perfusion pressure value with said knowledge base to generate a cross referenced data result indicative of said severity and stage of lower extremity disease.

9. A system for assessing severity and stage of lower extremity disease comprising:
at least one blood flow sensor that measures skin perfusion pressure;
a knowledge base that provides data on a plurality of lower extremity angiosomes;
a processing device in operable communication with said at least one blood flow sensor and said knowledge base, said processing device configured to output a visual representation of at least one of said plurality of lower extremity angiosomes to guide said at least one blood flow sensor in mapping of a testing site relative to a target vessel;
an inflatable cuff, wherein said at least one blood flow sensor is in communication with the cuff for measuring blood flow in a patient;
a pressure sensor in communication with the cuff for reading pressure levels in the cuff;
a pressure instrument in fluid communication with the cuff for inflation and deflation thereof, the pressure instrument comprising:
a source of pressurized air; and
a conduit connected to the source of pressurized air and the cuff, thereby placing the source of pressurized air in fluid communication with the cuff, wherein said processing device is operably coupled to said pressure instrument and capable of controlling pressurized airflow to and from the cuff, and further wherein said processing device is arranged to receive inputs from said at least one blood flow sensor and said pressure sensor;
a computer program executable by the processing device such that when executed, the computer program causes the processing device to:
initiate an automatic inflation sequence resulting in a no flow condition;
initiate an automatic deflation sequence;
automatically qualify a perfusion measurement as a skin perfusion pressure value upon all conditions of a set of predetermined conditions being met during the deflation sequence,
wherein said processing device receives said skin perfusion pressure value based on angiosome mapping, and cross references said skin perfusion pressure value with said knowledge base to generate a cross referenced data result indicative of a severity and stage of peripheral arterial disease and wound healing potential.

* * * * *